(12) United States Patent
Cornelissen et al.

(10) Patent No.: US 11,667,980 B2
(45) Date of Patent: Jun. 6, 2023

(54) USE OF FCA CONTROL BASED ON PH

(71) Applicant: Novozymes A/S, Bagsvaerd (DK)

(72) Inventors: Sjef Cornelissen, Bagsvaerd (DK);
Benny Cassells, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 370 days.

(21) Appl. No.: 16/636,747

(22) PCT Filed: Aug. 7, 2018

(86) PCT No.: PCT/EP2018/071311
§ 371 (c)(1),
(2) Date: Feb. 5, 2020

(87) PCT Pub. No.: WO2019/030186
PCT Pub. Date: Feb. 14, 2019

(65) Prior Publication Data
US 2020/0216920 A1 Jul. 9, 2020

(30) Foreign Application Priority Data
Aug. 7, 2017 (EP) .................................... 17185048

(51) Int. Cl.
| | | |
|---|---|---|
| *C12Q 1/00* | (2006.01) | |
| *C12Q 3/00* | (2006.01) | |
| *C12N 1/20* | (2006.01) | |
| *C12Q 1/02* | (2006.01) | |

(52) U.S. Cl.
CPC ............... *C12Q 3/00* (2013.01); *C12N 1/20* (2013.01); *C12Q 1/025* (2013.01)

(58) Field of Classification Search
CPC ........................................................ C12Q 3/00
See application file for complete search history.

(56) References Cited

U.S. PATENT DOCUMENTS

| | | | | |
|---|---|---|---|---|
| 6,232,111 | B1 * | 5/2001 | Zhang ................ | C12N 1/16 435/254.22 |
| 6,284,453 | B1 * | 9/2001 | Siano ................. | C12N 1/38 435/243 |
| 2003/0124644 | A1 * | 7/2003 | Takano ............... | A61K 31/352 435/6.15 |
| 2009/0131782 | A1 * | 5/2009 | Moonen .............. | A61N 7/02 601/3 |
| 2015/0010899 | A1 | 1/2015 | Riisgaard et al. | |
| 2015/0140615 | A1 | 5/2015 | Park et al. | |

FOREIGN PATENT DOCUMENTS

| | | |
|---|---|---|
| CN | 1982467 A | 6/2007 |
| CN | 101333547 A | 12/2008 |
| CN | 104093846 A | 10/2014 |
| CN | 104487582 A | 4/2015 |

OTHER PUBLICATIONS

Lv et al (Biotechnology Letters vol. 26, pp. 1713-1716) (Year: 2004).*
Ahn et al, 2000, Appl Environ Microbiol 66(8), 3624-3627.
Akesson et al, 1999, Biotechnol Bioeng 64(5), 590-598.
Bader et al, 2007, Chemical and biochemical engineering quarterly 21(4), 315-320.
Garcia-Arrazola et al, 2005, Biochem Eng Journal 23(3), 221-230.
Henes et al, 2007, J Biotechnol 132(2), 118-126.
Johnsson et al, 2013, Biotechnol Progr 29(3), 817-824.
Johnsson, 2015, Lund University PhD thesis, 1-153.
Schaepe et al, 2014, J Biotechnol 192, 146-153.
Whiffin et al, 2004, Biotechnol Bioeng 85(4), 422-433.

* cited by examiner

*Primary Examiner* — Albert M Navarro
(74) *Attorney, Agent, or Firm* — Eric Fechter

(57) ABSTRACT

Disclosed is a method for controlling the carbon feed to a fed-batch fermenter based on the disturbance of the pH signal following the addition or a limiting substrate.

18 Claims, 4 Drawing Sheets

USE OF FCA CONTROL BASED ON PH

CROSS-REFERENCE TO RELATED APPLICATIONS

Figure 1:
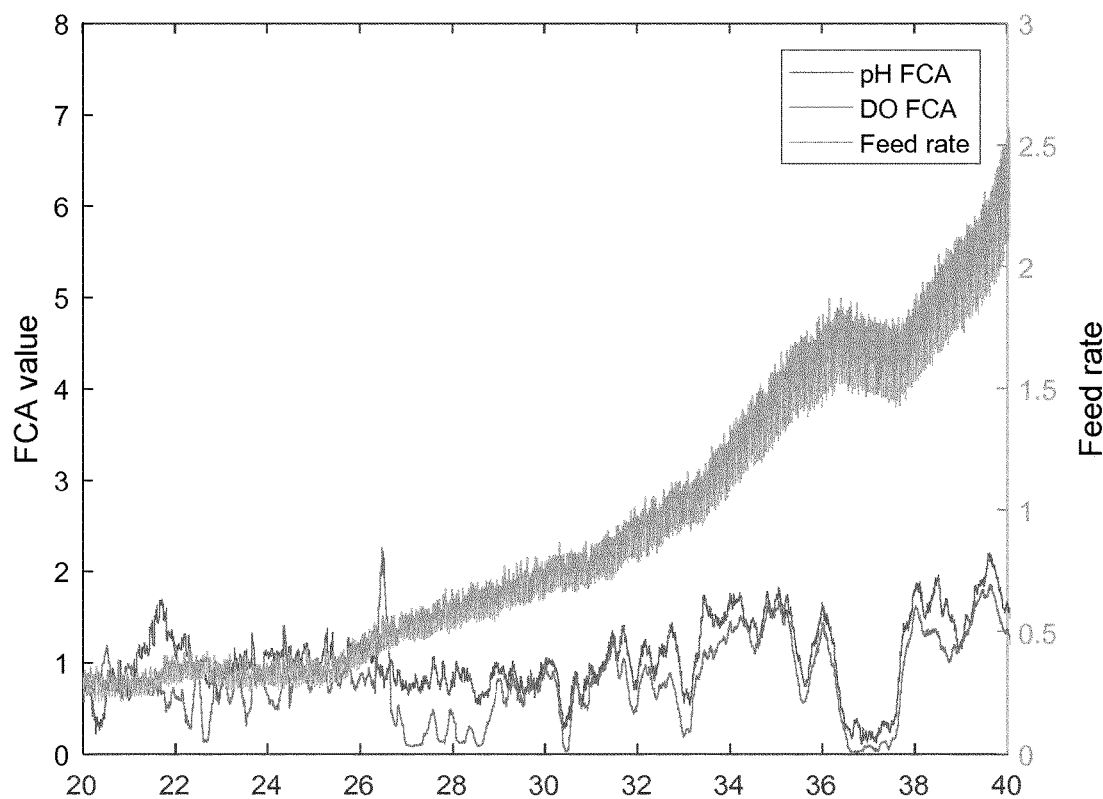

This application is a 35 U.S.C. 371 national application of PCT/EP2018/071311, filed Aug. 7, 2018, which claims priority or the benefit from European Patent Application No. 17185048.0, filed Aug. 7, 2017. The contents of these applications are fully incorporated herein by reference.

FIELD OF THE INVENTION

The present invention relates to industrial fermentation processes, in particular controlling the carbon feed in fed-batch fermentations.

BACKGROUND OF THE INVENTION

Bacterial and fungal microorganisms are workhorses for industrial microbiology as they are used for the commercial production of many different therapeutics (e.g. penicillin and cephalosporin), pharmaceutical proteins (e.g. insulin), polysaccharides (e.g. hyaluronic acid), enzymes (e.g. proteases), and commodity chemicals (e.g. citric acid).

In industry, it is very common to use a fed batch fermentation process. A fed batch fermentation is a process which is based on feeding of a growth limiting nutrient substrate to a culture. The growth limiting nutrient substrate is typically a carbohydrate, but it could in principle be any nutrient, e.g. the nitrogen source.

The rate of carbohydrate addition in a fed batch fermentation, wherein a microorganism produces a compound of interest or the microorganism itself is the product of interest, is a highly critical process parameter. Overfeeding of the carbohydrate has been shown to lead to loss of batches or severely lowered productivity due to, e.g., production of unwanted side products.

Different strategies have been used in order to control the growth in a fed batch process including perturbation based control, where you induce a perturbation in the fermenter and typically analyses the response in the dissolved oxygen (DO) in the fermentation broth.

One such perturbation based control strategy is Frequency content analysis (FCA) which is a method to find the maximum carbon dosing rate in a fermentation without overdosing the cells and having to deal with undesired overflow metabolites such as acetate. The FCA signal is obtained by pulsing the carbon source and subsequently analyzing the response in the dissolved oxygen (DO) signal. A lack of response in the DO signal indicates that the dosing rate exceeds the culture's substrate uptake capacity. In this case, the cells will not completely oxidize the carbon source but form unwanted byproducts that can negatively affect growth and production of a desired fermentation product. A large response in the DO signal indicates that the culture oxidizes the added carbon rapidly followed by a rapid decrease in dissolved oxygen.

Typically, in FCA control the feed pulses are increased when the FCA signal exceeds a defined fix-point and decreased when the FCA is below the fix-point, thereby controlling the carbon feed to the cultures capacity to metabolize the carbon source and preventing overfeed.

[M. Åksson et al. 1999, Biotech. Bioeng. 64(5):590-598; O. Johnsson 2015, PhD thesis, Perturbation-based control of industrial fed-batch bioprocesses, Lund University], disclosed that by tracking the DO response to the pulses over time and adjusting the dosing rate accordingly, acetate formation in the culture can be prevented DO and oxygen uptake rate (OUR) have been used for dosing control using the perturbation method [M. Åksson et al. 1999, Biotech. Bioeng. 64(5):590-598; V. S. Whiffin et al. 2004, Biotech. Bioeng. 85(4):422-433; B. Henes & B. Sonnleiter 2007, J. Biotech. 132:118-126; S. Schaepe et al. 2014, J. Biotech. 192:146-153; O. Johnsson 2015, PhD thesis, Perturbation-based control of industrial fed-batch bioprocesses, Lund University].

SUMMARY OF THE INVENTION

The invention provides a method for controlling the carbon feed to a fed-batch fermentation comprising adding an aliquot of a limiting substrate to the fermentation broth, measuring the disturbance in the pH of the fermentation broth and adjusting the carbon feed in response to the magnitude of the disturbance of the pH signal.

DETAILED DESCRIPTION OF THE INVENTION

It is known in the art that the rate of carbohydrate addition in, e.g., a *Bacillus* fed batch fermentation is a highly critical process parameter. Overfeeding of a substrate has been shown to lead to loss of batches or lowered carbon utilization efficiency. It is therefore important to have reliable methods available for controlling the feed in fed batch fermentation to enable the highest possible productivity without overfeeding.

This invention presents a method for monitoring and controlling the microbial carbon utilization efficiency in fermentation processes whereby it is possible to optimize the process without risking overfeeding and need to have detailed information about the strain's growth characteristics.

In the art the DO and oxygen uptake rate (OUR) have been used for dosing control using the perturbation method described above [M. Åksson et al. 1999, Biotech. Bioeng. 64(5):590-598; V. S. Whiffin et al. 2004, Biotech. Bioeng. 85(4):422-433; B. Henes & B. Sonnleiter 2007, J. Biotech. 132:118-126; S. Schaepe et al. 2014, J. Biotech. 192:146-153; 0. Johnsson 2015, PhD thesis, Perturbation-based control of industrial fed-batch bioprocesses, Lund University].

However, we found that analysis of the pH signal can be used for this purpose as well. This is surprising because the pH value is controlled at a set value during the entire fermentation and therefore it is not obvious that pH value responds to pulses of the feed rate and reveals useful information about the physiological state of the culture.

According to the invention the carbon feed in a fed-batch fermentation is controlled by inducing a process disturbance by adding an aliquot of a limiting substrate and measuring the disturbance in the pH of the fermentation broth and adjusting the carbon feed in response to the magnitude of the disturbance of the pH signal.

The term "carbon feed" is according to the invention intended to mean a solution comprising a carbon source that is fed to the fermenter during the fed-batch phase of the fermentation process. The carbon feed will deliver the necessary carbon source to the microorganisms for growth and optionally producing a product of interest.

The term "limiting substrate" is according to the invention intended to mean a nutrient that is required for growth of the microorganism. Examples of limiting nutrients include nitrogen sources, such as ammonia, urea, nitrate; and carbon sources such a carbohydrates e.g. glucose, sucrose, dextrose, lactose; where the carbon sources are preferred.

The addition of the aliquot of the limiting substrate leads to an uptake and metabolism of the limiting substrate by the microorganism and this is also reflected in the pH of the fermentation, where the pH of the fermentation broth is affected by the disturbance and gradually returns to the pH value before the aliquot of limiting substrate was added. It is believed that the metabolic activity of the microorganisms is the factor that triggers the pH signal, meaning that if the addition of the limiting substrate induces a high increase in metabolic activity a large pH signal is seen whereas if the addition of the limiting substrate gives rise to a small or even no increase in metabolic activity only a small if any impact of the pH signal is seen. Because metabolic activity requires an available carbon source the carbon feed is according to the invention controlled based on the perturbations in the pH signal caused by addition of a limiting substrate. This means that if a large pH signal is observed following addition of a limiting substrate indicating a high increase in the metabolic activity the carbon feed is increased and if a small pH signal is observed following addition of a limiting substrate the carbon feed is reduced. In this way will the control according to the invention secure that the addition of carbon feed is high when the metabolic activity in the microorganisms is high meaning that they can convert high amounts of carbon source and the carbon feed is low when the metabolic activity in the microorganisms is low and they therefore don't convert very much carbon source.

The limiting substrate and the carbon feed may be provided to the fermenter in the same or in separate solution(s). If the limiting substrate is a carbon source it is preferred that the carbon feed is the stream delivering the limiting substrate.

In one preferred embodiment the limiting substrate is added in pulses delivered with regular intervals to the fermentation or added in an oscillating but continuous mode, and where the magnitude of the carbon feed is determined by the pH signal.

In this embodiment it is convenient to process the pH signal by Fourier transformation as known in the art. A Fourier transformation of the pH signal reveals a frequency spectrum of oscillations that together make up the pH signal. By analyzing the spectrum at the frequency at which the limiting substrate is being fed to the fermenter, the response of the limiting substrate pulses on the metabolic activity of the microorganisms can be quantified. This response is being characterized as the FCA-value. The larger the response of the pH signal is to the limiting substrate pulses, the higher the FCA values will be.

In a particular preferred embodiment the limiting substrate is included in the carbon feed the control is performed In a way that if a given pulse, or a peak in the feed if the limiting substrate is added in an oscillating but continuous mode, gives rise to a small change in the pH signal then the next pulse, or peak in the feed if the limiting substrate is added in an oscillating but continuous mode, will be small, meaning only a small amount of carbon feed is added, whereas if the pulse, or a peak in the feed if the limiting substrate is added in an oscillating but continuous mode, gives rise to a large change in the pH signal the next pulse, or peak in the feed if the limiting substrate is added in an oscillating but continuous mode, will be large, meaning that a large amount of carbon feed is added.

When the FCA value is used for regulation of the carbon feed to the fermentation a set-point for the FCA-value is typically defined for the fermentation, if the measured FCA-value is higher than the set-point the carbon feed is increased, if the measured FCA-value is below the set-point the carbon feed is reduced.

It is within the skills of the average practitioner to define a suitable set-point for a given fermentation, based on the specific conditions and signal treatment used for the particular fermentation.

This is all known in respect of perturbation-based control of industrial fed-batch bioprocesses, in particular FCA based control of fermentation processed, based on DO and the techniques known in respect of such control mechanisms apply also for the methods of the present invention with the exception that the methods of the invention is based on the pH signal and not an oxygen signal.

The methods of the invention have several benefits compared with the corresponding methods using oxygen based perturbation control methods:

The methods of the invention are more robust and can control the fermentation process satisfactory during irregularities e.g. in stirring, oxygen supply and pressure/backpressure;

Online pH and DO measurements are standard in the fermentation industry, where pH measurements can be considered more reliable than DO measurements. Oxygen uptake rate (OUR) measurement relies on specialized equipment (e.g. a mass spectrometer) that is not standard equipment in every fermentation facility. Furthermore, to calculate the FCA value through Fast Fourier Transformation, frequent sampling is needed in order to capture the oscillations in the pH and/or DO signals. For some types of oxygen electrodes, high frequency measurements can reduce the lifetime of the probes, whereas the measurement frequency does not affect the life time of the pH electrode;

The methods of the invention can be used under situations where oxygen based perturbation control methods can not be used such as under oxygen limited conditions.

The methods of the invention are particular suited for fermenting a microorganism for the production of a product of interest, or the microorganism itself may be the product of interest.

Microorganisms

The microorganism used according to the invention may be any microorganism known in the art that can be cultivated in a fermentor, or it may even be a mixture or two or more of such microorganisms.

The microorganism according to the invention may be a bacterial strain, e.g., a Gram-positive strain such as a *Bacillus, Clostridium, Enterococcus, Geobacillus, Lactobacillus, Lactococcus, Oceanobacillus, Staphylococcus, Streptococcus*, or *Streptomyces* strain, or a Gram-negative strain such as a *Campylobacter, Escherichia, Flavobacterium, Fusobacterium, Helicobacter, Ilyobacter, Neisseria, Pseudomonas, Salmonella*, or *Ureaplasma* strain.

In one aspect, the strain is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* strain; in particular the strain is a *Bacillus licheniformis* strain.

In another aspect, the strain is a *Streptococcus equisimilis, Streptococcus pyogenes, Streptococcus uberis*, or *Streptococcus equi* strain.

In another aspect, the strain is a *Streptomyces achromogenes, Streptomyces avermitilis, Streptomyces coelicolor, Streptomyces griseus*, or *Streptomyces lividans* strain.

The microorganism may be a fungal strain. For example, the strain may be a yeast strain such as a *Candida, Kluyveromyces, Pichia, Saccharomyces, Schizosaccharomyces*, or *Yarrowia* strain; or a filamentous fungal strain such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* strain.

In another aspect, the strain is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* strain.

In another aspect, the strain is a yeast strain, e.g., a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* strain.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The microorganism may be an organism that naturally produces the product of interest or it may be a microorganism that have been genetically altered to produce the product of interest e.g. by inserting a gene encoding the product on interest under control of suitable control elements to secure the production of the gene. Methods for constructing an organism producing an product of interest is known in the art and such methods are also suitable for the present invention.

Compound of Interest

The compound of interest according to the invention may be a polypeptide e.g. a therapeutic polypeptide such as insulin; or a peptide, or a protein such as an enzyme The compound of interest may also be a polysaccharide such as hyaluronic acid, an antibiotic such as penicillin or cephalosporin or erythromycin, or a commodity chemical such as citric acid.

A preferred peptide according to this invention contains from 2 to 100 amino acids; preferably from 10 to 80 amino acids; more preferably from 15 to 60 amino acids; even more preferably from 15 to 40 amino acids.

In a preferred embodiment, the compound of interest is an enzyme, in particular a hydrolase (class EC 3 according to Enzyme Nomenclature; Recommendations of the Nomenclature Committee of the International Union of Biochemistry).

In a particular preferred embodiment the following enzymes are preferred aminopeptidase, amylase, amyloglucosidase, mannanase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, lysozyme, muramidase, xanthanase or xylanase.

Proteases: Suitable proteases include those of animal, vegetable or microbial origin. Microbial origin is preferred. Chemically modified or protein engineered mutants are included. The protease may be an acid protease, a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE™ SAVINASE™, PRIMASE™, DURALASE™, ESPERASE™, RELASE™ and KANNASE™ (Novozymes NS), MAXATASE™, MAXACAL™, MAXAPEM™, PROPERASE™ PURAFECT™, PURAFECT OXP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™, LIPOLASE ULTRA™ and LIPEX™ (Novozymes NS).

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, WO 97/43424, and WO 01/66712, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™, NATALASE™, TERMAMYL LC™, TERMAMYL SC™, LIQUIZYME-X™ and BAN™ (Novozymes NS), RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYME™, CAREZYME™, and CAREZYME CORE™ (Novozymes NS), CLAZINASE™, and PURADAX HA™ (Genencor International Inc.), and KAC-500(B)™ (Kao Corporation).

Pullulanases: Pullulanases include those of bacterial or fungal origin. Chemically modified or protein engineered mutants are included.

The pullulanase according to the present invention is preferably a pullulanase from e.g. *Pyrococcus* or *Bacillus*, such as *Bacillus acidopullulyticus*, e.g., the one described in Kelly et al., 1994, *FEMS Microbiol. Letters* 115: 97-106; or a pullulanase available from Novozymes NS such as Promozyme™.

The pullulanase may also be from *Bacillus naganoencis*, or *Bacillus deramificans*, e.g., such as derived from *Bacillus deramificans* (U.S. Pat. No. 5,736,375).

Oxidoreductases: Oxidoreductases include those of bacterial or fungal origin. Chemically modified or protein engineered mutants are included. Oxidoreductases include peroxidases, and oxidases such as laccases, and catalases.

Other preferred hydrolases are carbohydrolases including MANNAWAY™. Other preferred enzymes are transferases, lyases, isomerases, and ligases.

Fermentations

Accordingly, the present invention may be useful for any fermentation having a culture medium in micro scale and up to any fermentation having a culture medium in industrial scale, e.g., typically of from 1000 liters to 500.000 liters.

The microorganism may be fermented by any method known in the art, provided that a limiting substrate is being added. The fermentation medium may be a complex medium comprising complex nitrogen and/or carbon sources, such as soybean meal, soy protein, soy protein hydrolysate, cotton seed meal, corn steep liquor, yeast extract, casein, casein hydrolysate, potato protein, potato protein hydrolysate, molasses, and the like. The fermentation medium may be a chemically defined media, e.g. as defined in WO 98/37179.

Carbon Sources

The present invention may be useful for any metabolizable carbon source.

A carbohydrate or carbon source selected from the group consisting of glucose, sucrose, fructose, maltose, lactose, maltulose, mannose, glycerol, and galactose is preferred; in particular a carbon source selected from the group consisting of glucose, sucrose, lactose, glycerol and maltose is preferred.

Recovery of the Compound of Interest

A further aspect of the invention concerns the downstream processing of the fermentation broth. After the fermentation process is ended, the compound of interest may be recovered from the fermentation broth, using standard technology developed for the compound of interest.

The relevant downstream processing technology to be applied depends on the nature of the compound of interest.

A process for the recovery of a compound of interest from a fermentation broth will typically (but is not limited to) involve some or all of the following steps:
1) pre-treatment of broth (e.g. flocculation)
2) removal of cells and other solid material from broth (primary separation)
3) filtration
4) concentration
5) stabilization and standardization.

Apart from the unit operations listed above, a number of other recovery procedures and steps may be applied, e.g., pH-adjustments, variation in temperature, crystallization, treatment of the solution comprising the compound of interest with active carbon, use of chromatography, and use of various adsorbents.

The invention is further illustrated in the following example which is not intended to be in any way limiting to the scope of the invention as claimed.

EXAMPLES

Materials and Methods

Microorganism: A *Bacillus licheniformis* strain was transformed with copies of the gene encoding *Bacillius lentus* protease (Savinase) gene, inserted as described in WO 02/00907

Fermentation: A pilot scale fermentor (ca. 1 m$^3$), equipped with pO$_2$ and pH probes, was use for the examples. The fermenter containing medium was inoculated with a seed culture (appx. 15% of medium volume) and fermentation was started with aeration and constant stirring and carbon feed medium was added controlled as specified in the examples.

Medium:

The carbon-limited medium in the fermenter was selected for optimal growth and product formation and contained a complex nitrogen source, inorganic salts (at least including: $Na^+$, $Ca^{2+}$, $K^+$, $Mg^{2+}$, $SO_4^{2-}$, $PO_4^{3-}$) and trace elements. The carbon source was added during the fermentation and the carbon feed medium consisted of a highly concentrated sugar solution.

After preparing the medium, it was sterilized for by heat treatment and cooled down to 38° C. and the pH adjusted to the desired value.

Seed Culture:

The seed culture was prepared in a pilot scale seed fermenter (ca. 1 m³). The medium consisted of a complex carbon and nitrogen source and inorganic salts (including $PO_4^{3-}$). The mixture was sterilized by heat treatment and, after cooling down to 37° C., the pH was adjusted to the desired value. Stirring and aeration was initiated and the microorganism inoculated and fermentation was continued until the culture has a satisfactory cell density.

Example 1 Using FCA Based on pH Signal for Controlling Fermentations

A seed fermentation was performed as described above and used to inoculate 4 identical main fermenters with standard medium.

After inoculation the carbon feed was started at a low feed rate of 0.3 l/h. The carbon source was fed in pulses with a fixed pause between the pulses of 150 s. This gives rise to oscillations in both the dissolved oxygen (DO) and pH signals.

A Fourier transformation of the pH signal reveals the frequency of the oscillation that can be found in the pH signal. The response at a frequency of 6.7 mHz corresponds to the frequency at which the carbon source is being fed to the fermenter. This response is being characterized as the FCA-value. The larger the response of the pH signal is to the carbon feed pulses, the higher the FCA values will be.

A set-point of 0.5 was defined for this experiment, if the measured FCA-value is higher than the set-point the feed rate is increased, if the measured FCA-value is below the set-point the feed rate is reduced.

All 4 fermentations gave a reproducible exponential feed rate, demonstrating that FCA control based on pH signal is providing a reliable method for controlling the feed in a fed-batch fermentation.

Example 2. Comparison Between pH and DO FCA Values

The pH and DO based FCA-values for one of the four batches described in example 1 were calculate and drawn in the same graph, see FIG. 1.

The comparison shows that the signals are very similar meaning that under normal conditions, there are no major difference between the two calculated FCA-values and they can both be used for controlling the feed rate in fermentations.

Example 3. Response of DO and pH Based FCA Values to Process Disturbances

In this example a fermentation was conducted as described in example 1. The feed rate was switched to a fixed rate when the DO reached a value of 20% and process disturbances were initiated.

Figure 2A:
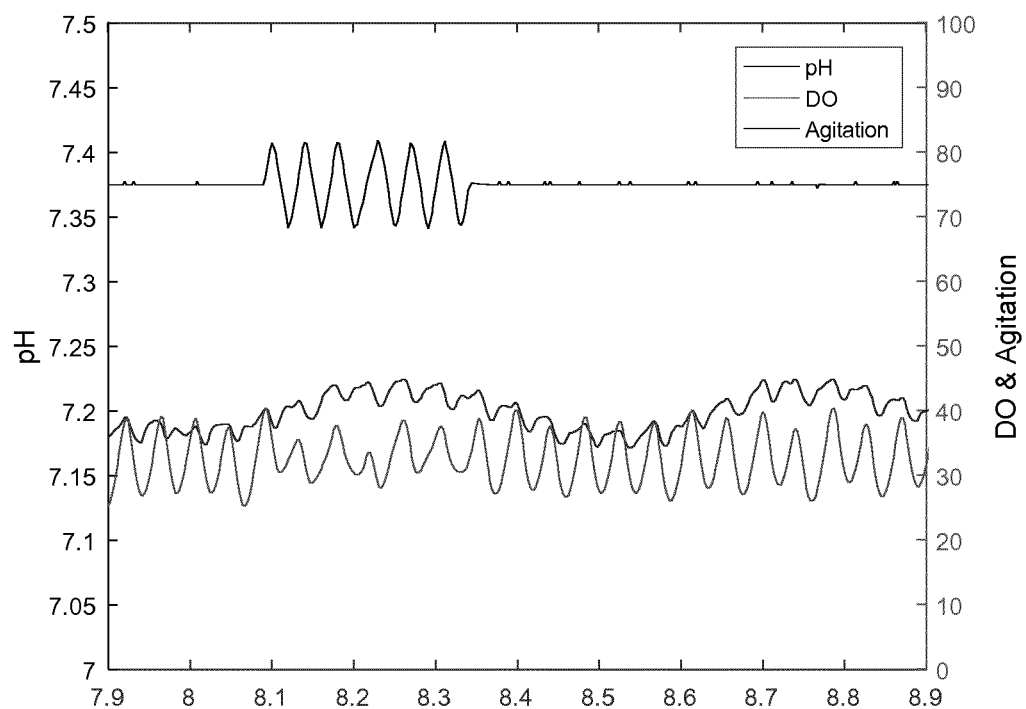
Figure 2B:
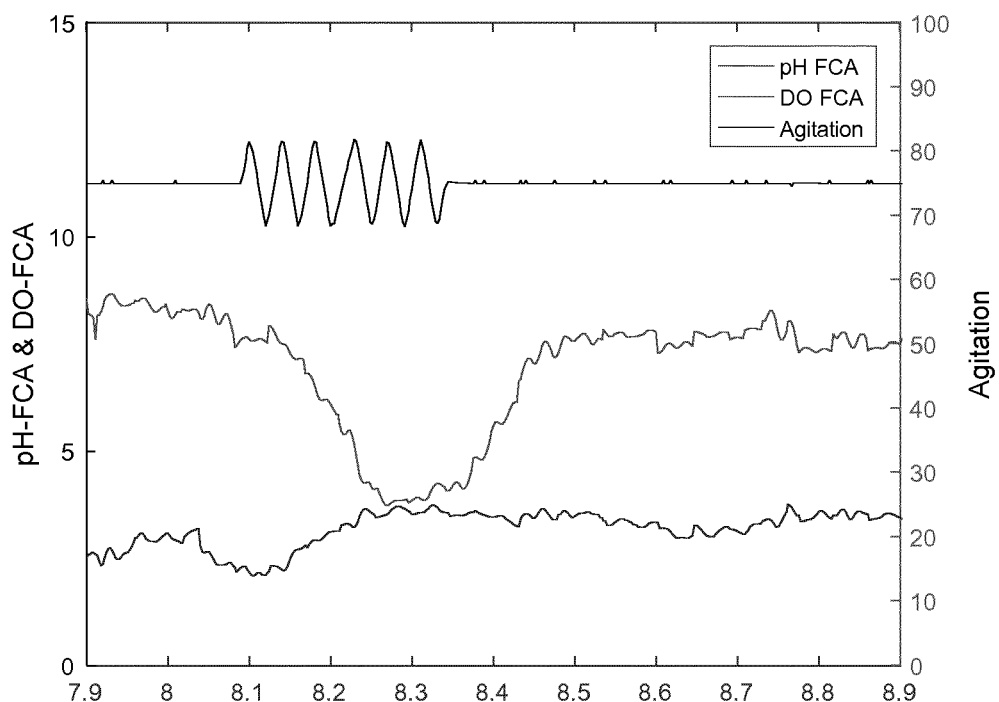

In this example the fermentation was disturbed by oscillating the agitation speed+/−10%. The frequency of the disturbance was 6.7 mHz, the same as the frequency of the carbon feed pulses. The effect of the disturbances are shown in FIG. 2A and the FCA-values based on DO and pH are shown in FIG. 2B.

The results show that the FCA values based on DO drops by ca. 50% and recovers after the disturbance is over, whereas the FCA values based on pH are not affected in a high degree. This means that if the feed rate was controlled by the DO-based FCA-value the feed would have been significantly reduced by the disturbance, whereas it would have been largely unaffected if it was controlled by the pH based FCA-values.

Example 4. Response of DO and pH Based FCA Values to Process Disturbances

In this example a fermentation was conducted as described in example 1. The feed rate was switched to a fixed rate when the DO reached a value of 20% and process disturbances were initiated.

In this example the fermentation was disturbed by oscillating the backpressure+/−10%. The frequency of the disturbance was 6.7 mHz, the same as the frequency of the carbon feed pulses.

Figure 3A:
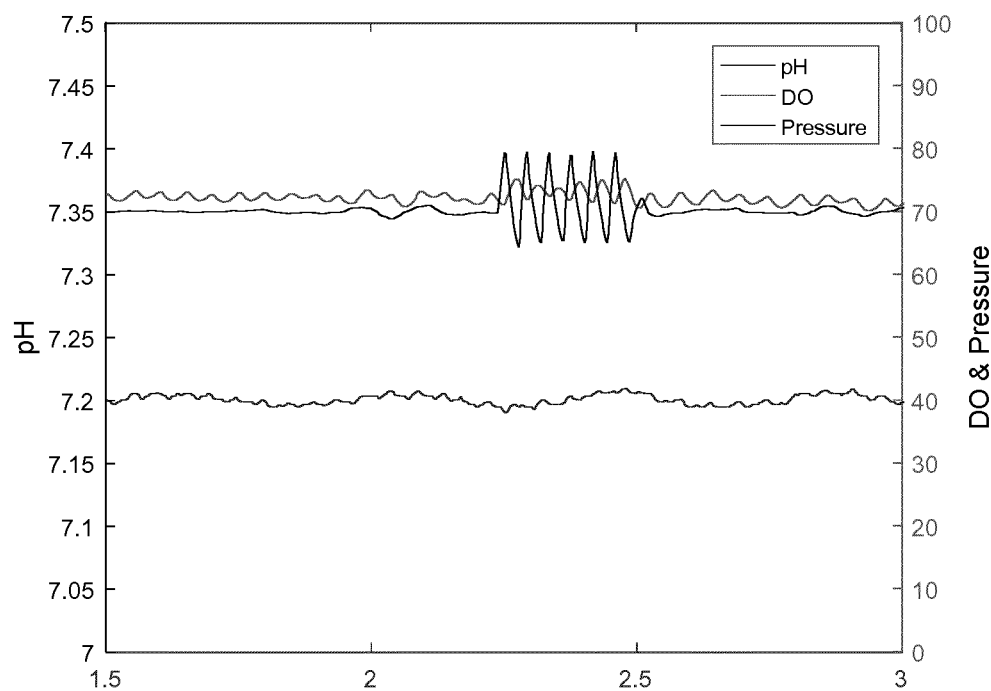
Figure 3B:
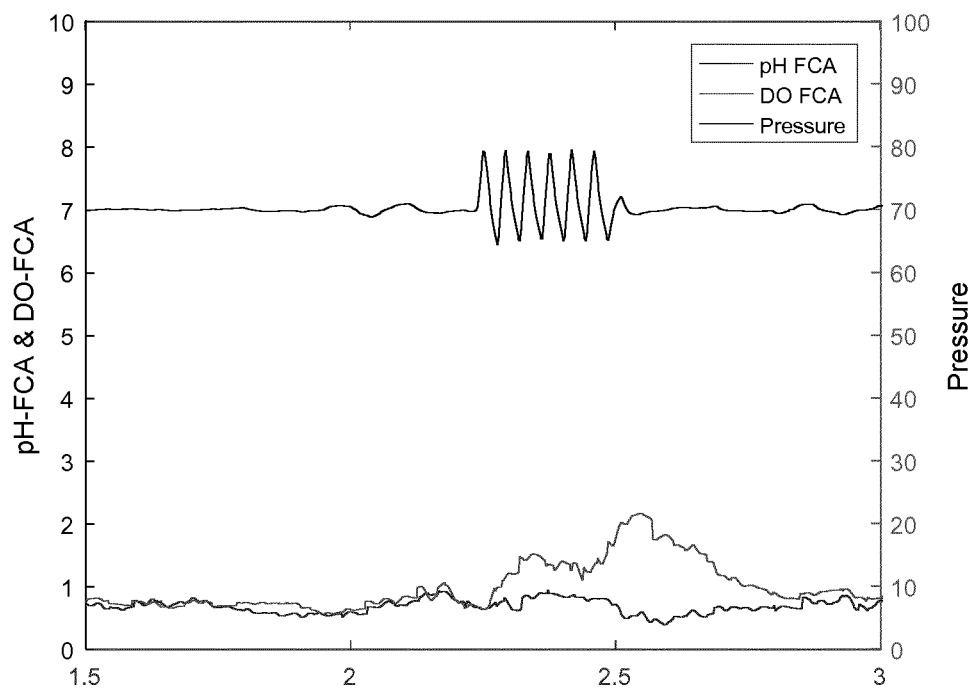

The effect of the disturbances are shown in FIG. 3A and the FCA-values base on DO and pH are shown in FIG. 3B.

The results show that the FCA values based on DO are almost doubled and recovers after the disturbance is over, whereas the FCA values based on pH are not affected in a high degree. This means that if the feed rate was controlled by the DO-based FCA-value the feed would have been significantly increased by the disturbance, whereas it would have been largely unaffected if it was controlled by the pH based FCA-values.

Example 5—FCA Controlled Fermentation Under Oxygen Limited Conditions

In this example a fermentation was conducted as described in example 1. The feed rate was switched to a fixed rate when the DO reached a value of 20% and agitation lowered to establish oxygen limited conditions.

Figure 4A:
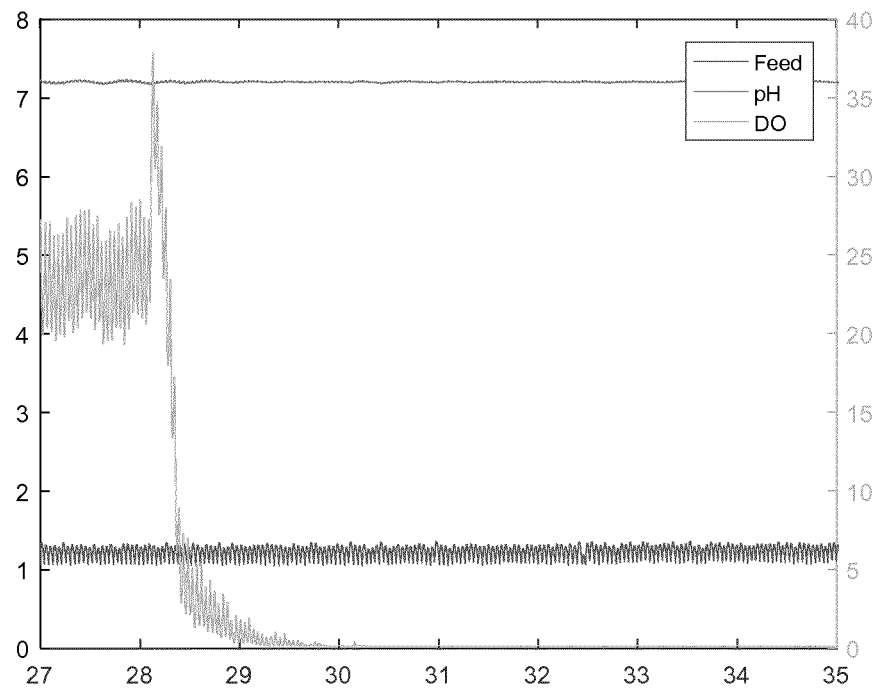
Figure 4B:
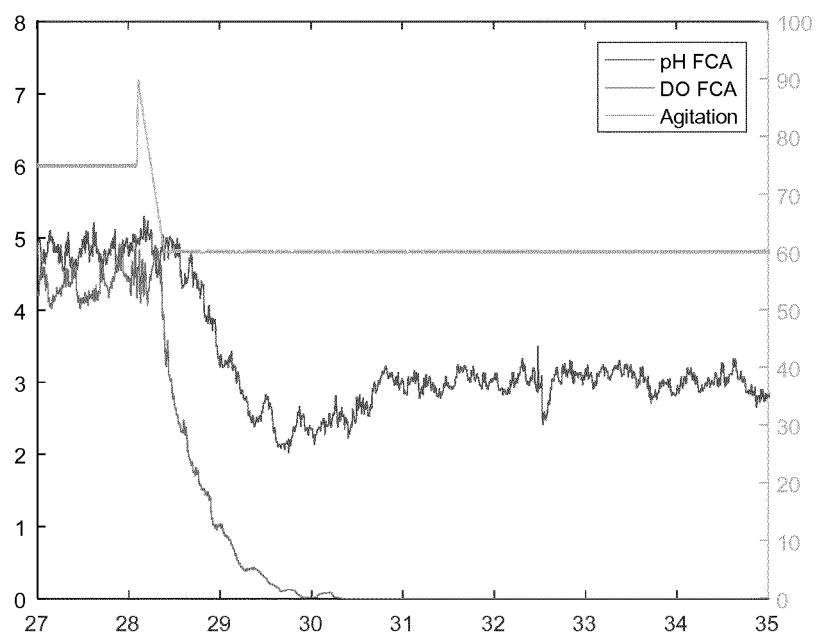

The DO and pH were measured and are shown in FIG. 4A, and the FCA-values based on DO and pH were calculated and are shown in FIG. 4B.

The results show that the DO decreased to about 0% immediate after the reduced agitation and the FCA-value based on DO followed the DO to 0, which means that FCA-value based on DO is not useable for controlling the feed rate under these conditions.

The FCA-value based on pH was reduced to a lower level (presumably because the metabolic activity of the cell also was reduced due to the oxygen limitation), but despite the lower level the FCA value could easily be measured reflecting the metabolic activity of the microorganisms under these conditions.

Thus, the example clearly demonstrate that FCA based on pH can be determined under oxygen limited conditions, whereas FCA based on DO fails under these conditions.

The invention claimed is:

1. A method for controlling the carbon feed to a fed-batch fermentation, the method comprising adding an aliquot of a limiting substrate to the fermentation broth, measuring the disturbance in the pH of the fermentation broth and adjusting the carbon feed in response to the magnitude of the disturbance of the pH signal, wherein the limiting substrate is a carbon source and the limiting substrate is the same as the carbon source in the carbon feed, wherein fermentation is a fermentation of one or more microorganisms for the production of one or more products of interest, wherein the one or more microorganisms are selected from bacterial strains and fungal strains, and wherein the carbon feed is added in discrete pulses supplied with regular intervals (at a regular frequency) or added in an oscillating but continuous mode, and the magnitude of the pH signal is used for controlling the carbon feed.

2. The method of claim 1, wherein the pH signal is treated by Fourrier transformation revealing the frequency of the oscillation of the pH signal, and the magnitude of the pulses, or the peaks if the carbon feed is added in an oscillating but continuous mode, is increased when the Fourrier transformed pH signal at the frequency identical to the frequency of the feed pulses or the frequency of the feed oscillation, exceeds a fixed value and decreased when the Fourrier transformed pH signal at the frequency identical to the frequency of the feed pulses, or the frequency of the feed oscillation, is below the fixed value.

3. The method of claim 1, wherein the one or more microorganisms is one or more bacterial strains.

4. The method of claim 3, wherein the one or more microorganisms are selected from *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, Bacillus thuringiensis, Streptococcus equisimilis, Streptococcus pyogenes, Streptococcus uberis, Streptococcus equi Streptomyces achromogenes, Streptomyces avermitilis, Streptomyces coelicolor, Streptomyces griseus*, and *Streptomyces lividans* strains.

5. The method of claim 1, wherein the one or more microorganisms is one or more fungal strains.

6. The method of claim 5, wherein the strains are selected from *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei, Trichoderma viride, Saccharomyces carlsbergensis, Saccharomyces cerevisiae, Saccharomyces diastaticus, Saccharomyces douglasii, Saccharomyces kluyveri, Saccharomyces norbensis*, and *Saccharomyces oviformis* strains.

7. The method of claim 1, wherein the one or more products comprise one or more proteins.

8. The method of claim 7, wherein the one or more proteins is one or more enzymes.

9. The method of claim 1, wherein the carbon feed comprises at least 10% carbon source.

10. The method of claim 1, wherein the volume of the fermenter is at least 20 liter.

11. The method of claim 1, wherein the fermentation is run under conditions where oxygen limitation occur under at least part of the fermentation.

12. The method of claim 3, wherein the one or more bacterial strains is selected from Gram-positive strains *Bacillus, Clostridium, Enterococcus, Geobacillus, Lactobacillus, Lactococcus, Oceanobacillus, Staphylococcus, Streptococcus*, and *Streptomyces* strains.

13. The method of claim 3, wherein the one or more bacterial strains is selected from Gram-negative strains *Campylobacter, Escherichia, Flavobacterium, Fusobacterium, Helicobacter, Ilyobacter, Neisseria, Pseudomonas, Salmonella*, and *Ureaplasma* strains.

14. The method of claim 5, wherein the one or more fungal strains is one or more yeast strains.

15. The method of claim 14, wherein the one or more yeast strains is selected from yeast strains *Candida, Kluyveromyces, Pichia, Saccharomyces, Schizosaccharomyces*, and *Yarrowia* strains.

16. The method of claim 5, wherein the one or more fungal strains is one or more filamentous fungal strains.

17. The method of claim 16, wherein the one or more filamentous fungal strains is selected from filamentous fungal strains *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, and *Xylaria* strains.

18. The method of claim 8, wherein the one or more enzymes is selected from aminopeptidase, amylase, amyloglucosidase, mannanase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, lysozyme, muramidase, xanthanase and xylanase.

* * * * *